United States Patent [19]

Kulas

[11] 4,417,873
[45] Nov. 29, 1983

[54] DENTAL ARTICULATOR

[76] Inventor: Walenty Kulas, 35 Amherst Ave., Feeding Hills, Mass. 01030

[21] Appl. No.: 285,597

[22] Filed: Jul. 21, 1981

[51] Int. Cl.³ .......................................... A61C 11/00
[52] U.S. Cl. ..................................... 433/57; 433/54; 433/66
[58] Field of Search ...................... 433/54, 57, 58, 59, 433/60, 61, 62, 63, 64, 65, 66, 67, 68

[56] References Cited

U.S. PATENT DOCUMENTS

| | | | |
|---|---|---|---|
| 1,848,267 | 3/1932 | Perkins | 433/58 |
| 2,269,061 | 1/1942 | Nerbas | 433/65 |
| 2,270,561 | 1/1942 | Sanborn | 433/63 |
| 2,275,726 | 3/1942 | Burns et al. | 433/65 |
| 2,600,899 | 6/1952 | McClain | 433/63 |
| 2,608,761 | 9/1952 | Scott | 433/58 |
| 2,617,195 | 11/1952 | Perkell et al. | 433/65 |
| 2,765,533 | 10/1956 | McMorris | 433/60 |
| 2,930,127 | 3/1960 | Mann et al. | 433/56 |
| 3,815,242 | 6/1974 | Martfay et al. | 433/63 |
| 3,930,312 | 1/1976 | Daub | 433/61 |

Primary Examiner—John J. Wilson
Attorney, Agent, or Firm—Donald S. Holland

[57] ABSTRACT

A dental articulator or apparatus is disclosed for testing the accuracy of dentures during occlusion. The articulator is designed to simulate the complex three-dimensional motion of a human jaw and includes a longitudinally-extending base, an upper denture carrier pivotally mounted above the base for movement in a vertical plane, and a lower denture carrier pivotally connected to the base by a bearing-and-slot arrangement that permits three-dimensional curvilinear movement of the lower carrier. By attaching dentures to the carriers and moving the dentures through various centric, eccentric, lateral and protrusive movements against one another, the articulator permits "high spots" on the occlusal surfaces of the dentures to be located so that the dentures can be accurately ground to a proper fitting.

4 Claims, 4 Drawing Figures

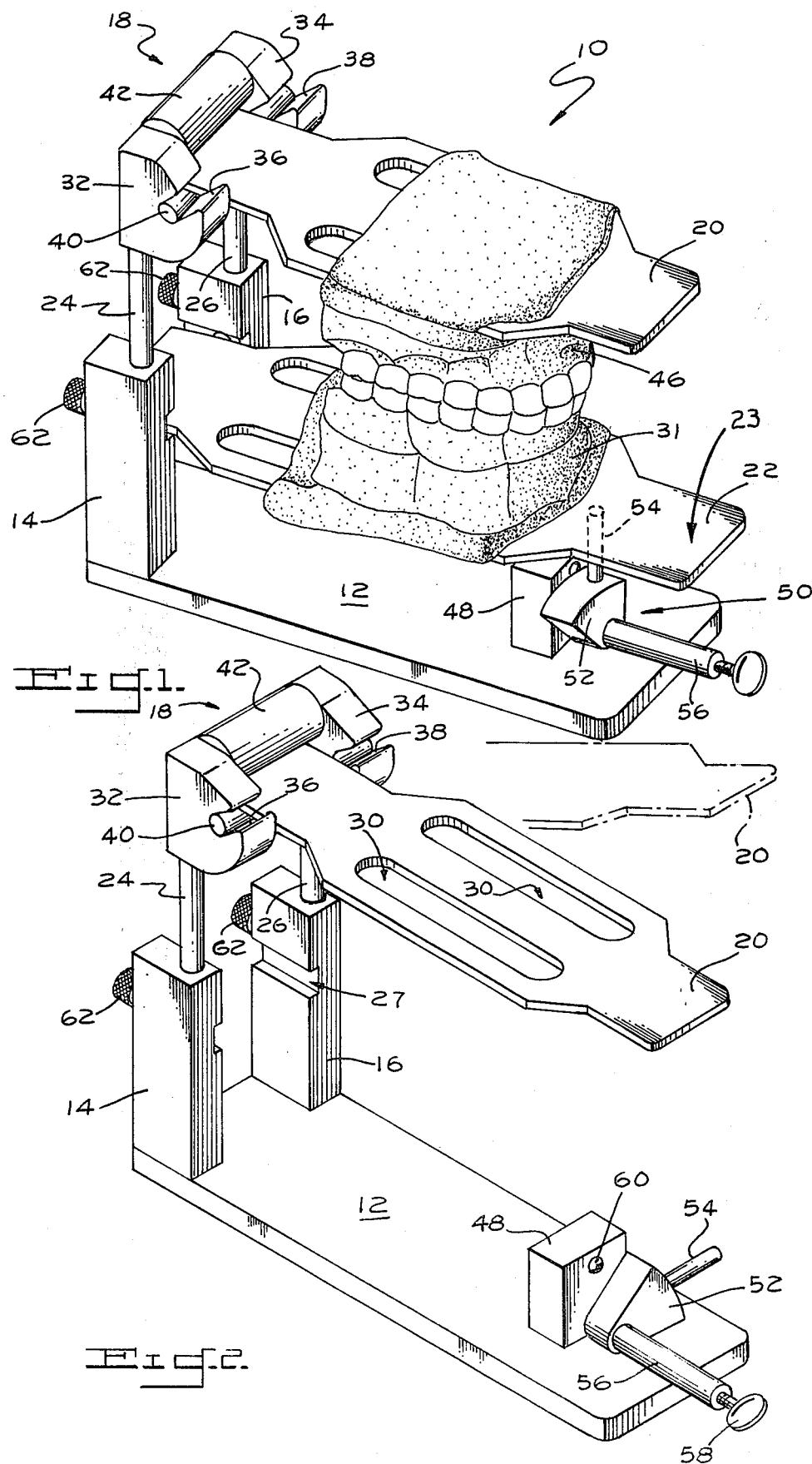

DENTAL ARTICULATOR

BACKGROUND OF THE INVENTION

The present invention relates to dental equipment and more particularly relates to "dental articulators".

Dental articulators are used by lab technicians to determine whether a set of dentures need to be ground to fit properly in a wearer's mouth. Articulators generally have upper and lower movable carriers on which the dentures are mounted with their teeth facing one another. By moving the carriers so that the dentures ride against one another in various occlusal movements, the technician can observe "high spots" on the dentures, which he can later grind to produce a more accurate fitting. If the carriers can be constructed so that their movements are able to simulate the complex three-dimensional movements of the human mandible, virtually all of the "high spots" on the occlusal surfaces can be eliminated so that the dentures will fit comfortably and properly in a wearer's mouth during all of the varied jaw movements. The simulated movement thus enables a technician to manufacture accurate dentures without the need of guesswork or trial-and-error fittings of the dentures in the wearer's mouth.

Several attempts have been made to produce an articulator that can simulate the varied jaw motions, e.g., see U.S. Pat. Nos. 1,848,267; 2,270,561; 2,617,195; and 2,765,533. However, these attempts have generally resulted in complicated apparatus that have upper and lower denture carriers with very limited freedom of movements. Consequently, the prior articulators generally do not simulate the movements of the human jaw and, therefore, do not faultlessly test a set of dentures.

Accordingly, it is a primary object of the present invention to provide a dental articulator which will simulate the complex movements of the human jaw to permit an accurate grinding of the occlusion of dentures so that the dentures will fit properly in a wearer's mouth during all of the varied jaw movements.

It is another object to provide a dental articulator for completely and efficiently testing the accuracy of dentures, enabling the operator to investigate fully the extent to which the dentures are suited to one another and able to serve their purpose.

It is another object to provide a dental articulator which will eliminate guesswork and simplify the heretofore hit-and-miss nature of grinding a proper bearing surface for dentures.

It is a further object to provide a durable articulator that is extremely simple to operate.

These and objects of the invention will become readily apparent when reference is made to the following description taken in conjunction with the accompanying drawings.

BRIEF DESCRIPTION OF THE DRAWINGS

FIG. 1 is a perspective side view of a dental articulator constructed in accordance with the present invention, wherein the articulator has two dentures mounted on it for inspection;

FIG. 2 is a perspective view of the articulator, similar to FIG. 1, but with the dentures and a lower denture carrier removed;

DETAILED DESCRIPTION OF THE PREFERRED EMBODIMENTS

Figure 3:
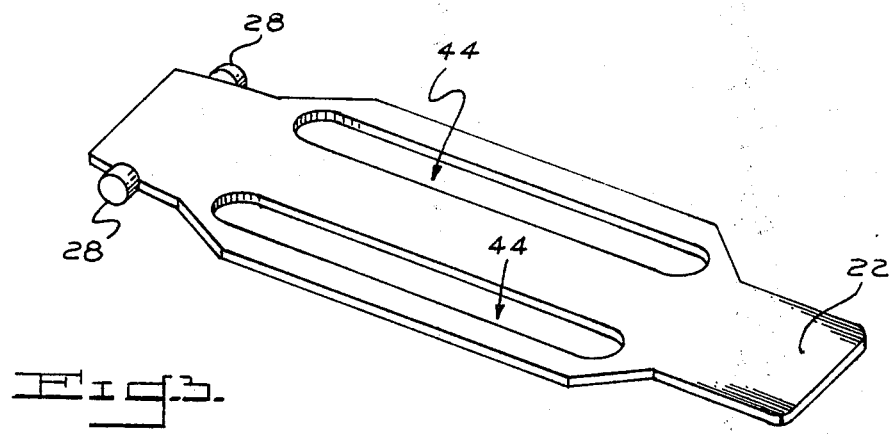
FIG. 3 is a perspective top view of the lower denture carrier.

Referring to the drawings in detail, a dental articulator for testing the occlusal movements of dentures is shown in FIG. 1 and generally designated by the reference numeral 10. The articulator includes a longitudinally-extending base 12 having a pair of upstanding columns 14, 16 at one end thereof, a hinge unit 18 that is telescopically mounted on the columns, an upper denture carrier 20 that is pivotally attached to the unit 18 for movement in a vertical plane relative to the base (see the phantom lines in FIG. 2), and a lower denture carrier 22 that is pivotally attached between the columns by a bearing-and-slot arrangement that permits three-dimensional curvilinear movement of the lower denture carrier.

As best shown in FIGS. 1 and 2, the base 12 is made of any suitable material such as brass or bronze. Its columns 14, 16 each include a vertically-extending bore (not shown) for telescopically receiving a pair of spaced support rods 24, 26 from the hinge unit 18, as well as a transverse slide channel or slot 27 for removably receiving a bearing 28 from each side of the lower denture carrier 22.

Referring to FIG. 3, the lower carrier 22 is a flat piece with a pair of longitudinal, elongated openings or gaps 44 through which plaster of Paris, or the like, can be poured to help secure a lower denture 31 to the carrier (see FIG. 1). The bearings 28, which attach the carrier to the columns are rounded trunnion pins and permit the carrier to be freely pivoted side to side in the slots 27. Further, they permit the carrier to freely move forwardly and rearwardly in the slots, as well as pivot vertically. This combined three-way freedom of movement enables the carrier to be manually moved in a three-dimensional, curvilinear movement which resembles the varied motions of the lower jaw.

Hinge unit 18 comprises a pair of spaced C-blocks 32, 34 that are attached to the parallel support rods 24, 26. The blocks have upwardly opening notches 36, 38 adapted to pivotally receive a hinge bar 40 that is attached to the underside of the upper denture carrier 20. A transverse flange 42 interconnects the blocks and acts as a stop means to prevent the carrier from pivoting below a plane that is substantially parallel to the base 12.

Upper carrier 20 is a flat piece that, like lower carrier 22, has a pair of elongated gaps or openings 30 to assist in attaching a denture 46 to it by plaster of Paris or the like. The hinge bar 40 of this carrier is removable from the pivot blocks 32, 34 so that the upper denture can be easily positioned or removed.

As best shown in FIGS. 1 and 2, the base 12 has a resting post 48 for the lower carrier. A detent 50 is pivotally attached to the post and can be used to lock the lower carrier in a fixed position parallel to the base.

The detent 50 comprises a pivotable lock body 52 with an attached pin 54 that mates with a recess (not shown) in the bottom of the lower carrier to hold the carrier (and denture) in place when the pin is in an upright position. A shaft 56 extends from the lock body and has a thumbscrew 58 at one end that can be turned to easily pivot the shaft, lock body and pin.

When the pin is pivoted to its upright position, a lug 60 on the resting post 48 engages an indentation in the lock body to gently hold the body in place. To free the lower carrier for movement, the screw 58 is rotated to detach both the lug 60 from the lock body and the pin from the carrier.

Figure 4:
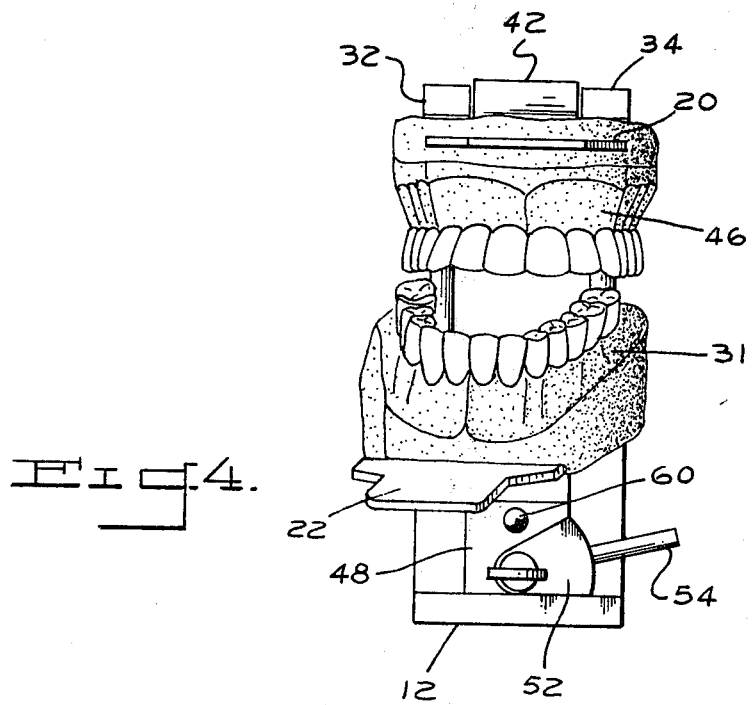
FIG. 4 is a front elevational view of the articulator, showing a set of dentures during testing.

To check the proper chewing and biting movements of the lower denture 31 against the upper denture 46, the upper carrier is maintained in a parallel position to the base 12, while the lower carrier is moved through its three-dimensional, jaw-like movements (see FIG. 4).

As should be understood by those skilled in the art, the lower carrier 22 is moved by gripping its fore portion 23 between the user's thumb and forefinger and then freely moving the lower carrier (in the slots 27) through all of the various lower jaw movements. Since the bearing-and-slot arrangement 28, 27 permits the lower carrier to accurately simulate the complex three-dimensional movements of the human mandible, the attached dentures 31, 46 ride against one another in normal occlusal movements, just as they would in a wearer's mouth.

By using standard "articulator" paper ("high spot" indicating paper) between the dentures, a technician can readily locate virtually all of the "high spots" on their occlusal surfaces. He can then eliminate the spots by milling so that the dentures will fit comfortably and properly in the wearer's mouth during all of the various jaw movements.

In the preferred embodiment, the parallel rods 24, 26 that support the hinge unit 18 are held in their respective column bores by a pair of set screws 62 (see FIGS. 1 and 2). By loosening the screws and raising or lowering the rods, the height of the hinge unit 18 can be selectively adjusted so that the articulator 10 can be fit to various size dentures.

In another embodiment of the invention (though not shown), the lower carrier 22 is interconnected to the base 12 by a detachable spring to both secure the lower carrier to the base and to return the lower carrier to its proper position after movement.

While two different embodiments have been expressly described, it will be understood by those skilled in the art that obvious structural modifications can be made without departing from the spirit and scope of the invention. For example, while the bearings 28 have been disclosed as stationary pins, they could, of course, be small rollers to assist in movement of the lower carrier in the slots 27. Accordingly, reference should be primarily made to the following claims, rather than to the detailed description of the preferred embodiments, to determine the scope of the invention.

Having thus described the invention, what is claimed is:

1. A dental articulator comprising:
   (a) a longitudinally-extending base;
   (b) a pair of spaced columns rising perpendicularly from the base;
   (c) means for supporting a first denture horizontally above the base, said means comprising an upper longitudinally-extending carrier that is pivotally attached to said columns for movement in a vertical plane, said carrier being adapted to be positioned horizontally above the base or swung away from the base;
   (d) means attached to the columns for selectably adjusting the height of the upper carrier above the base;
   (e) means for supporting a second denture above the base, between the base and said upper carrier, said means comprising a lower longitudinally-extending carrier that is adapted to support the second denture in an opposed relationship to the first denture; and
   (f) means for permitting three-dimensional movement of the lower carrier, while the carrier is in the articulator, to simulate the movement of a human lower jaw, said means comprising a pair of rounded trunnion pins that extend from opposite sides of said lower carrier into respective, transverse and substantially straight grooves in said columns that are stationary relative to said columns and substantially parallel to one another, said grooves each being elongated and having a length substantially greater than the diameter of each pin, whereby the lower carrier can be swiveled freely side-to-side in the grooves, can be moved forwardly and rearwardly in the grooves a distance substantially greater than the diameter of either pin, and can be pivoted vertically toward or away from the base.

2. The dental articulator of claim 1 wherein the articulator includes a means for locking the lower carrier in a fixed position that is parallel to the base so that the second denture is held stationary while the first denture can be pivoted away from and against said second denture.

3. The dental articulator of claim 2 wherein the locking means includes a pivotable pin that engages a recess in said lower carrier.

4. A dental articulator comprising:
   (a) a longitudinally-extending base;
   (b) a pair of spaced columns rising perpendicularly from the base;
   (c) means for supporting a first denture horizontally above the base, said means comprising an upper longitudinally-extending carrier that is detachably connected to said columns;
   (d) means for supporting a second denture above the base, between the base and said upper carrier, said means comprising a lower longitudinally-extending carrier that is adapted to support the second denture in an opposed relationship to the first denture; and
   (e) means for permitting three-dimensional movement of the lower carrier, while the carrier is in the articulator, to simulate the movement of a human lower jaw, said means comprising a pair of rounded trunnion pins that extend from opposite sides of said lower carrier into respective, transverse and substantially straight grooves in said columns that are stationary relative to said columns and substantially parallel to one another, said grooves each being elongated and having a length substantially greater than the diameter of each pin, whereby the lower carrier can be swiveled freely side-to-side in the grooves, can be moved forwardly and rearwardly in the grooves a distance substantially greater than the diameter of either pin, and can be pivoted vertically toward or away from the base.

* * * * *